United States Patent
Applegate et al.

(10) Patent No.: US 8,114,622 B2
(45) Date of Patent: Feb. 14, 2012

(54) METHODS FOR GENERATION OF REPORTER PHAGES AND IMMOBILIZATION OF ACTIVE BACTERIOPHAGES ON A POLYMER SURFACE

(75) Inventors: Bruce Michael Applegate, West Lafayette, IN (US); Lynda Louise Perry, Bothell, WA (US); Mark Thomas Morgan, West Lafayette, IN (US); Aparna Kothapalli, Minneapolis, MN (US)

(73) Assignee: Purdue Research Foundation, West Lafayette, IN (US)

( * ) Notice: Subject to any disclaimer, the term of this patent is extended or adjusted under 35 U.S.C. 154(b) by 174 days.

(21) Appl. No.: 12/549,500

(22) Filed: Aug. 28, 2009

(65) Prior Publication Data

US 2010/0075301 A1    Mar. 25, 2010

Related U.S. Application Data

(60) Provisional application No. 61/093,004, filed on Aug. 29, 2008.

(51) Int. Cl.
   C12Q 1/70   (2006.01)
   C12Q 1/66   (2006.01)
   C12N 15/79  (2006.01)

(52) U.S. Cl. .............. 435/8; 435/320.1; 424/9.1
(58) Field of Classification Search .............. None
   See application file for complete search history.

(56) References Cited

OTHER PUBLICATIONS

Waddell et al. FEMS Microbiology Letters 2000, vol. 182, pp. 285-289.*
Gamage et al. Infection and Immunity, 2004, vol. 72, No. 12, pp. 7131-7139.*
Mole et al. Journal of Chemical Technology and Biotechnology 2001, vol. 76, pp. 683-688.*

* cited by examiner

*Primary Examiner* — Bao Li
(74) *Attorney, Agent, or Firm* — Miller, Matthias & Hull LLP

(57) ABSTRACT

Novel reporter bacteriophages are provided. Provided are compositions and methods that allow bacteriophages that are used for specific detection or killing of *E. coli* 0157:H7 to be propagated in nonpathogenic *E. coli*, thereby eliminating the safety and security risks of propagation in *E. coli* 0157:H7. Provided are compositions and methods for attaching active bacteriophages to the surface of a polymer in order to kill target bacteria with which the phage comes into contact. Provided are modified bacteriophages immobilized to a surface, which capture *E. coli* 0157:H7 and cause the captured cells to emit light or fluorescence, allowing detection of the bacteria in a sample.

12 Claims, 4 Drawing Sheets

METHODS FOR GENERATION OF REPORTER PHAGES AND IMMOBILIZATION OF ACTIVE BACTERIOPHAGES ON A POLYMER SURFACE

RELATED APPLICATIONS

This application claims the benefit of U.S. Provisional Application Ser. No. 61/093,004, filed Aug. 29, 2008, the entire contents of which is hereby incorporated by reference.

GOVERNMENT INTERESTS

This invention was made with United States government support, specifically, Grant No. 58-1935-4-430, awarded by the USDA and Grant No. NAGS-12686, awarded by NASA. The United States government may have certain rights in this invention.

FIELD OF THE DISCLOSURE

This application relates to the fields of genetic engineering, molecular biology, and microbiology. In particular, this application relates to the use of bacteriophages in assays and processes.

BACKGROUND

Bacteriophages are viruses that infect bacteria. Bacteriophages, also called phages, may have a lysogenic cycle or a lytic cycle. Lysogenic phages are phages that can enter one of two alternative paths when infecting a cell: their DNA can integrate into the host DNA and replicate along with it, creating a lysogen; or the lytic cycle can occur instead. In the lytic cycle, once the phage has infected a bacterial cell, many copies of phage DNA are made, followed by synthesis of many phage capsids. The DNA is packaged in the capsids, the cell is lysed (broken open and destroyed) by phage enzymes, and the new phages are released. Lysogenic phages are sometimes called temperate phages. By contrast, a lytic phage is only capable of the lytic cycle, i.e., bacterial cells are lysed and destroyed after immediate replication of the viral particle and the new phages are released to find new hosts. Lytic phages do not create a lysogen. Lytic phages are sometimes called virulent phages.

Using recombinant DNA technologies, bacteriophage DNA can be manipulated to result in the expression of reporter genes in target, infected bacteria. Such methods have the potential of being very useful in detection assays. The lysogenic bacteriophage ΦV10 infects and reproduces in the pathogenic *E. coli* O157:H7. There remains a need for the large scale propagation of phages in non-pathogenic *E. coli*, thereby avoiding the safety and security risks of propagation in the pathogenic *E. coli* O157:H7. As contemplated herein, such large scale propagation of phages may enable the creation of anti-bacterial polymers for applications such as packaging materials for food or implantable medical devices. In addition, contemplated herein are methods for detection of *E. coli* in samples using bacteriophage immobilized on polymer film, thereby avoiding the traditional need of various reagents for detection.

BRIEF SUMMARY OF THE DISCLOSURE

Provided are compositions and methods for the generation of reporter phage via genetic manipulation of lysogenic ΦV10 for targeted detection of viable *E. coli* O157:H7 cells. In one embodiment, target bacteria are detected in a sample after infection with phage manipulated to include a colorimetric reporter.

Provided are compositions and methods for the propagation of *E. coli* O157:H7-specific bacteriophage in non-pathogenic *E. coli*. In certain embodiments, large scale propagation of *E. coli* O157:H7-specific bacteriophage occurs from lysogenic or lytic cycles in non-pathogenic *E. coli*.

Provided are compositions and methods for immobilizing active bacteriophages on a polymer surface. In one embodiment, UV polymerization is used for immobilization of phage on a polymer surface.

Provided are compositions and methods for *E. coli* O157:H7 detection using bacteriophage immobilized on a polymer film. In one embodiment, reporter-containing phage immobilized on a polymer is contacted with a target bacteria-containing sample, resulting in expression of the reporter and detection of the target bacteria.

DETAILED DESCRIPTION OF THE PREFERRED EMBODIMENTS

Unless defined otherwise, all technical and scientific terms used herein have the meaning commonly understood by a person skilled in the art to which this invention belongs. The following references provide one of skill with a general definition of many of the terms used in this invention: Singleton et al., 1994, Dictionary Of Microbiology And Molecular Biology, 2nd ed., John Wiley and Sons, NY; The Cambridge Dictionary Of Science And Technology, 1988, Walker ed., Cambridge University Press, Cambridge, UK; The Glossary Of Genetics, 1991, 5th ed., Rieger et al., eds., Springer Verlag, Berlin, Germany; and Hale and Markham, 1991, The Harper Collins Dictionary Of Biology, Harper Perennial, N.Y. As used herein, the following terms have the meanings ascribed to them unless specified otherwise.

Figure 1:
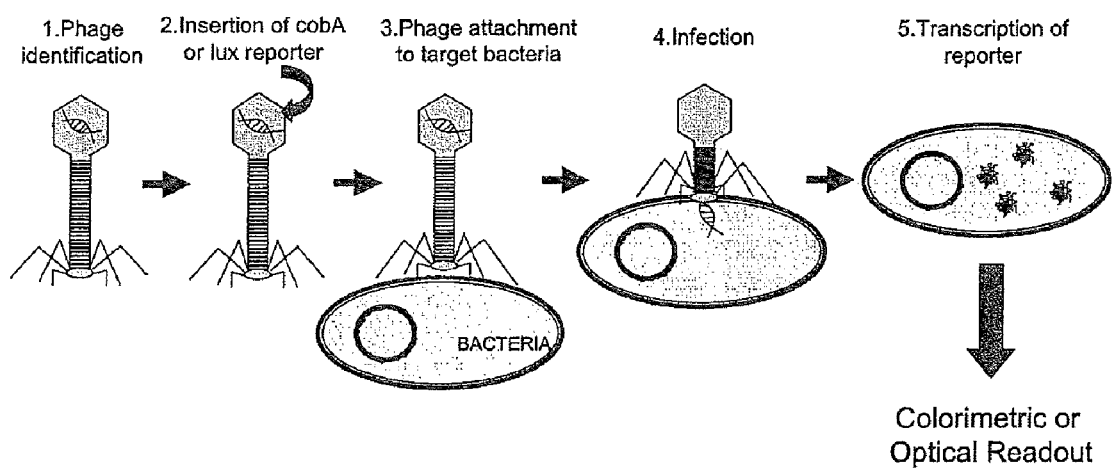
FIG. 1 schematically illustrates one embodiment of a bacteriophage assay.

Generation of Colorimetric Reporter Phage via Genetic Manipulation of Lysogenic ΦV10 for Targeted Detection of Viable *E. coli* O157:H7 Cells In one embodiment, provided is a colorimetric "reporter phage" to specifically detect viable *E. coli* O157:H7 in test samples. FIG. 1 illustrates the following five steps of this process: 1. Phage identification; 2. Insertion of a reporter; 3. Phage attachment to target bacteria; 4. Infection; and 5. Transcription of reporter. Ultimately, as also referenced in FIG. 1, expression of the reporter gene allows for a colorimetric or optical readout, thereby confirming detection. ΦV10, a lysogenic phage specific to *E. coli* O157:H7, has a completely sequenced genome, which facilitates genetic manipulation and conversion of ΦV10 to a reporter phage (see FIG. 1, step 1, phage identification). An *E. coli* O157:H7 detection system can be constructed using lysogenic phage because the prophage or phage genome allows for positive selection of recombinants through the use of antibiotic resistance genes. Characterization studies have demonstrated that the E. coli O157 antigen represents the targeting receptor for this ΦV10 phage and is a major determinant of its specificity. Acetylation of the E. coli O157 antigen by an enzyme encoded by a ΦV10 gene abolishes the ability of ΦV10 to infect an otherwise susceptible host.

The phage uses this surface O157 antigen to specifically target and identify a wide range of O157:H7 strains (see FIG. 1, step 3, phage attachment to target bacteria), including C7927, EDL933, 204P, and ATCC 43895 (a variant which constitutively produces curli fibers on its surface that could potentially block attachment and infectivity by ΦV10 but does not). This broad host infectivity is important because an ideal diagnostic assay should be able to detect all possible pathogenic strains of contaminating E. coli O157:H7 in both food and environmental testing samples.

Complete sequencing of the ΦV10 phage genome has identified recET, a putative non-essential gene, as an ideal target for gene replacement experiments. The λ-RED-based recombination system developed by Datsenko and Wanner was employed for the recET replacement procedure on the lysogenized ΦV10 phage (see FIG. 1, step 2, insertion of cobA or lux reporter). In order to gain a preliminary understanding of the replacement process, the inventors generated two constructs, one with a kanamycin resistance gene and one with both kanamycin resistance and cobA genes.

Characterization of the former construct, designated ΦV10 kan1, demonstrated the feasibility of this replacement strategy and provided a control. For this diagnostic tool to be functional in real pathogen detection scenarios, it is required that the modified "reporter" phage continues to retain its specific bacterial targeting and infectivity capability. Following replacement, the inventors harvested viable phage from a culture of modified ΦV10 lysogens and demonstrated potent and specific E. coli O157:H7 cell infectivity (see FIG. 1, steps 3 and 4, phage attachment to target bacteria and infection). Interestingly, ΦV10 kan1 plaques were very turbid compared to the wild type, to the extent that they can be rather difficult to see and enumerate. Without being bound by the following theory, it is possible that the ΦV10 kan1 plaques are very turbid because they have a high propensity to make lysogens, which may end up being more useful to this strategy, as lysogens are not killed by infection.

Propagation of E. coli O157:H7-Specific Bacteriophage in Non-Pathogens

Provided are compositions and methods that allow bacteriophages used for specific detection or killing of E. coli O157:H7 to be propagated on a large scale in non-pathogenic E. coli, thereby eliminating the safety and security risks of propagation in pathogenic E. coli O157:H7.

The lysogenic bacteriophage ΦV10 normally only infects E. coli O157:H7. However, as described herein, the ΦV10 lysogen of the non-pathogenic E. coli Top10 strain was isolated after introducing naked ΦV10 DNA into Top 10 by transformation. The ΦV10 DNA that was used to make the lysogen (E. coli Top10:ΦV10kan) had been previously modified by replacing the recET gene with a kanamycin resistance gene, which permitted the lysogen to be isolated by positive selection for kanamycin resistance. Similar lysogens can be isolated by transforming E. coli Top10 with DNA from reporter phage constructed as described below for the detection using bacteriophage immobilized in a polymer film. E. coli Top10:ΦV10kan does not spontaneously release active ΦV10 phage, probably because it is a recA mutant. Reporter phage can be synthesized and released from Top10 lysogens by manipulating the expression of the repressor, GP40, which is shown to be capable of repressing the lytic cycle. This can be done by creating a plasmid or genomic insert in which an antisense RNA complementary to the ribosome binding site of gene 40 is expressed from an inducible/repressible promoter, such as araC-Para, lacI$^q$-Plac, or λcI$^{857}$-P$_L$.

Induction or depression of the anti-sense RNA can trigger the lytic cycle in the lysogens, yielding a full burst of phage from each cell in the culture. Alternatively, the role of the anti-sense RNA could be played by an anti-repressor gene, analogous to λcro, if such a gene can be identified in ΦV10. Because the lysis genes will have been deleted from reporter phage, the lysis genes will have to be expressed from the inducible promoter as well.

In some embodiments, E. coli Top10:ΦV10kan can be modified to allow synthesis of phage which are capable of lytic propagation only. Such phage are suitable for use in phage therapy or creation of antibacterial polymers as detailed below. The repressor gene (gene 40) can be introduced into the lysogen on a plasmid or genomic insertional unit under the control of an inducible/repressible promoter, such as Para or Plac. The phage genomic copy of gene 40 is then deleted. Lysogeny will be maintained as long as gene 40 is induced, but repression of gene 40 will trigger entry into the lytic cycle, releasing a burst of progeny phage from each cell. The progeny phage, lacking the repressor gene, will be able to propagate lytically, but will not form lysogens. This is important because lysogens become immune to killing by the phage. Deletion of gene 40 can be accomplished by first using homologous recombination to replace gene 40 with an antibiotic resistance gene flanked by FLP recombinase recognition sites, then using FLP recombinase to delete the antibiotic resistance gene.

Method for Immobilizing Active Bacteriophages on a Polymer Surface

Provided are compositions and methods that allow active bacteriophages to get attached to the surface of a polymer in order to kill target bacteria with which they come into contact.

In an embodiment, a support polymer is corona treated to obtain a surface tension of greater than 45 dyne/cm. A mixture of trimethylolpropane triacrylate monomer, the photoinitiator methyl benzoylformate (2% wt/wt), and freeze-dried bacteriophage is applied to the support polymer surface and polymerized using a UV cross-linker to form a film containing embedded bacteriophage. The intensity of UV light used is approximately 3400 µW/cm$^2$ with a cure time ranging between 1-2 minutes under nitrogen atmosphere.

Figure 2:
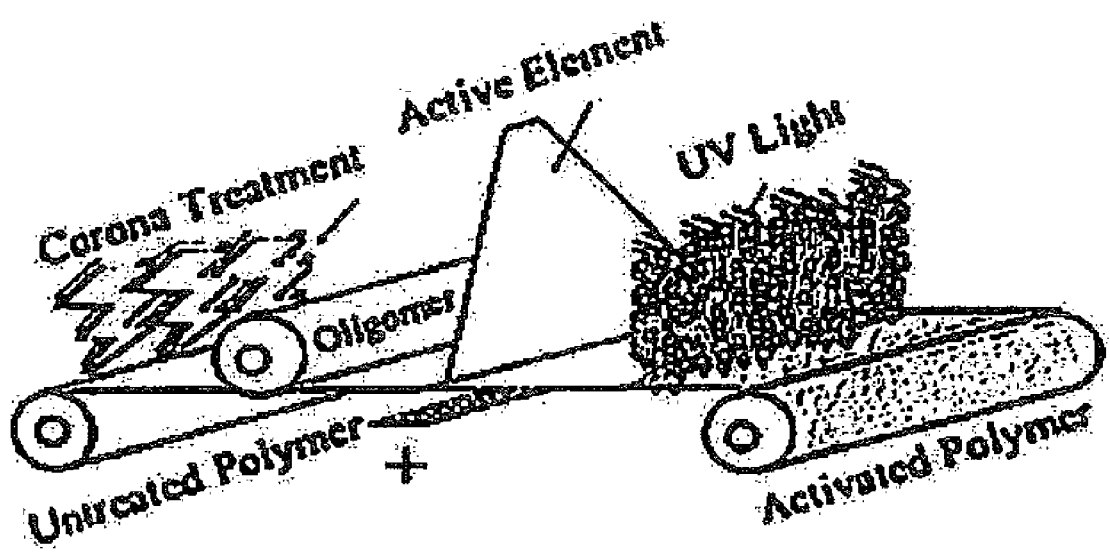
FIG. 2 schematically illustrates the UV polymerization process for the production of film-embedded bacteriophages.

FIG. 2 schematically illustrates the following steps of the UV polymerization process for the production of film-embedded bacteriophages: corona treatment, oligomer and active element application, and UV light exposure. The time required for polymerization depends on several factors including the type of UV lamp used, the intensity of light and the photoinitiator. Incorporating the bacteriophage in the cure mixture and subjecting to UV polymerization embeds the active element in the cured polymer matrix.

In one example, T4 bacteriophage were immobilized on a low density polyethylene coupon using the described procedure:

Immobilization Efficiency: The coupon with immobilized phage was washed with sterile water for 1 minute and phage in the wash were enumerated by plaque assay. It was observed that there was minimal loss of phage upon the first wash but there was no plaque forming units in the subsequent washes. This indicates that the immobilization is very effective and the first wash is sufficient in eliminating all the unbound phage (if any).

Activity of the immobilized phage: The activity of the immobilized phage against live E. coli cells in their log phase was tested by placing a coupon with immobilized phage onto the surface of a solid growth medium, then overlaying with molten top agar containing 100 µl E. coli cells/3 ml. No bacterial growth occurred in the vicinity of the coupon, indicating that immobilized phage are active and able to infect host bacteria.

Figure 3:
FIG. 3 shows images of petri dishes incubated with top agar overlay containing *E. coli* cells, one petri dish having a coupon with immobilized phage.

FIG. 3 shows images of the petri dishes incubated with top agar overlay containing E. coli cells. A coupon with immobilized T4 phage was included in the dish on the left. As described above, and in contrast to the petri dish on the right, no bacterial growth occurred in the area covered by the coupon. A control coupon coated with a film that lacked immobilized phage had no visible effect on bacterial growth (data not shown).

E. coli O157:H7 Detection using Bacteriophage Immobilized on a Polymer Film

Provided are modified bacteriophages immobilized to a surface, which capture E. coli 0157:H7 and cause the captured cells to emit light or fluorescence, thereby allowing detection.

Figure 4:
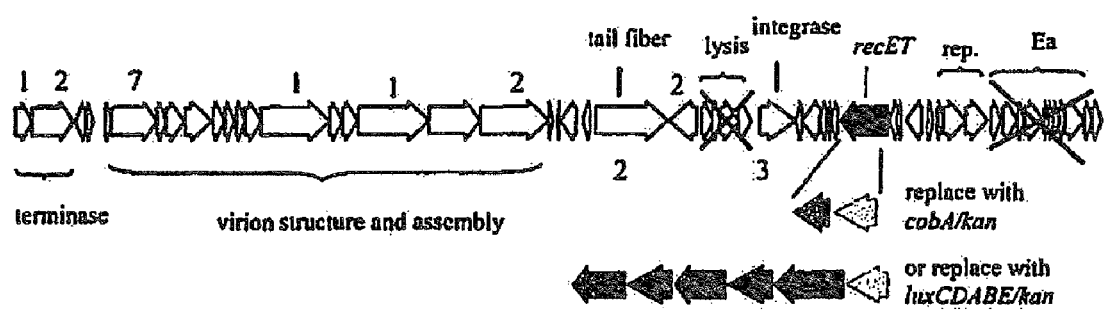
FIG. 4 schematically illustrates possible modifications to the bacteriophage ΦV10.

As described above, ΦV10 phage, a lysogenic phage specific for E. coli 0157:H7, can be modified by replacement of the non-essential gene recET with a cassette including a kanamycin resistance gene (to enable positive selection of recombinants) and a reporter gene or gene cluster such as the red fluorescent reporter cobA or the bioluminescent reporter luxCDABE. Gene replacement can be carried out in an E. coli 0157:H7 strain lysogenic for ΦV10 and can be accomplished by homologous recombination. It is necessary to remove additional non-essential DNA in order to achieve packaging of the luxCDABE modified phage. The phage lytic genes will be removed in order to prevent lysis of infected cells. The phage with this modification can be propagated as described above. Antibiotic resistance genes can generally be removed using the FLP recombinase once they have fulfilled their purpose of allowing positive recombinant selection. FIG. 4 illustrates modifications that can be made to ΦV10 phage.

In some examples, the recET gene of a ΦV10 lysogen has been successfully replaced by a kanamycin resistance gene. This lysogen spontaneously releases active bacteriophages that are capable of infecting E. coli 0157:H7, undergoing the lytic cycle, and forming lysogens. Lysogens containing the modified bacteriophage are resistant to kanamycin. The location of the kanamycin resistance gene in the position formerly occupied by recET has been confirmed by PCR.

In an embodiment, modified bacteriophage is immobilized to a discreet patch of a stomacher bag inner surface using the methods for immobilizing active bacteriophages to a polymer surface, as described above. For detection of E. coli O157:H7, a food sample can be mixed with a standard enrichment broth in a stomacher bag containing the immobilized reporter phage. If E. coli 0157:H7 are present, they will multiply in the enrichment broth and will also be captured and infected by the immobilized phage. Infection results in irreversible attachment of the bacterial cell to the immobilized phage, and also expression of the reporter genes. In turn, bioluminescence or red fluorescence appears on the stomacher bag surface where the phage are immobilized. Enrichment, capture, and detection are thereby accomplished simultaneously.

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters, obvious to those skilled in the art, are within the scope of this invention. All publications and patent applications cited herein are incorporated by reference in their entirety for all purposes.

What is claimed is:

1. A method of detecting the presence of a target bacterium in a sample, the method comprising:
   identifying a lysogenic phage specific to the target bacterium;
   inserting a polynucleotide encoding a reporter polypeptide into the phage,
   the reporter polypeptide being red fluorescent reporter cobA;
   contacting the phage with a preparation derived from the sample; and
   observing the expression or lack of expression of the reporter polypeptide, thereby detecting the presence or absence of the target bacterium in the sample.

2. The method of claim 1 wherein the expression of the reporter polypeptide is detected colorimetrically or optically.

3. The method of claim 1 wherein the target bacterium is E. coli O157:H7.

4. The method of claim 1 wherein the lysogenic phage is ΦV10.

5. The method of claim 4 wherein the recET gene of ΦV10 is replaced with the reporter polypeptide.

6. A method of detecting the presence of a target bacterium in a sample, the method comprising:
   providing a lysogenic phage specific to the target bacterium, wherein the lysogenic phage is immobilized on a polymer surface, and wherein the lysogenic phage comprises a polynucleotide encoding a reporter polypeptide, the reporter polypeptide being red fluorescent reporter cobA;
   contacting the lysogenic phage with a preparation derived from the sample; and
   observing the expression or lack of expression of the reporter polypeptide, thereby detecting the presence or absence of the target bacterium in the sample.

7. The method of claim 6 wherein the expression of the reporter polypeptide is detected colorimetrically or optically.

8. The method of claim 6 wherein the target bacterium is E. coli O15:H7.

9. The method of claim 6 wherein the lysogenic phage is ΦV10.

10. The method of claim 9 wherein the recET gene of ΦV10 is replaced with the reporter polypeptide.

11. The method of claim 6 wherein the sample is taken from food or beverage.

12. A kit comprising instructions and materials for carrying out the method of claim 6, including a polymer surface having a reporter polynucleotide-containing phage attached thereto.

* * * * *